United States Patent [19]

Armstrong

[11] Plant 4,195

[45] Jan. 24, 1978

[54] FLOWERING-FRUITING PEACH TREE

[75] Inventor: David L. Armstrong, Orange, Calif.

[73] Assignee: Armstrong Nurseries, Inc., Ontario, Calif.

[21] Appl. No.: 767,576

[22] Filed: Feb. 10, 1977

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Andrew R. Klein

[57] ABSTRACT

A new and very productive variety of flowering-fruiting peach tree, bearing an abundance of ornamental double flowers of strong reddish pink color in the last weeks of winter in Southern California, followed by a heavy crop of fairly large freestone fruits, which ripen on and after mid-July. The aroma and flavor of the fruit are strong, and the flesh is fine and tender, with melting texture and orange-yellow color. The growth habit of the tree is moderately vigorous, and its chilling requirement is slightly less than "Springtime".

2 Drawing Figures

The present invention relates to a new and distinct variety of peach tree of the yellow-fleshed, freestone, fruit-bearing and ornamental flowering type, which was originated by me as a seedling derived from crossing two unnamed and unpatented varieties, each of the latter being derived from an extended series of crosses involving the varieties "Luken's Honey" (unpatented), "Rio Oso Gem" (U.S. Plant Pat. No. 84), "Peppermint" (unpatented), "Flamingo" (U.S. Plant Pat. No. 661), "Helen Borchers" (unpatented), in the case of the seed parent, and "Luken's Honey" (unpatented), "Peppermint" (unpatented), "Socala" (unpatented), "Early Imperial" (unpatented), "Chinese Dwarf" (unpatented), "Coolidge Double Red" (unpatented), and "Rio Oso Gem" (U.S. Plant Pat. No. 84), in the case of the pollen parent.

The primary objective of this breeding was to broaden the spectrum of showy flower colors available during the blossoming season on trees which also produced good crops of good quality fruit. This was effected by selectively breeding the large, showy, double flower varieties of various flowering types of peaches, such as "Coolidge Double Red", "Peppermint", and "Helen Borchers", and selectively breeding for the fruit quality of the fruiting varieties of peaches such as "Rio Oso Gem", "Early Imperial", and "Socala". That this objective was achieved was evidenced by the following prominent features of my new variety, which represent a unique combination and distinguish the new variety from its parents, as well as from all other varieties of which I am aware:

1. A moderately vigorous habit of tree growth and a chilling requirement slightly less than that of "Springtime" peach (U.S. Plant Pat. No. 1,268);

2. Large, double flowers of medium red to dark pink color, borne generally in groups of 1 to 4 flowers per node, with the nodes relatively closely spaced, giving the tree a distinctive and highly ornamental appearance during the blooming period;

3. Large, yellow-fleshed, freestone fruit having a well-balanced, relatively strong peach flavor; and 4. Mid-season ripening of the fruit, generally beginning in mid-July and continuing through early August in the San Joaquin Valley of California.

The new variety more nearly resembles the variety "Double Delight" (U.S. Plant Pat. No. 1,787) than any other variety, but it is distinguished therefrom principally by its medium red to deep pink flowers, in contrast to the light pink flowers of "Double Delight"; also its fruit maturation period is from about a week to 10 days longer, on the average, than that of "Double Delight"; and it has a lower chilling requirement than "Double Delight."

Asexual reproduction of the new variety by budding, as performed at Wasco, Calif., shows that the foregoing characteristics and distinctions come true to form and are established and transmitted through succeeding asexual propagations.

The accompanying drawing shows typical specimens of the flowers, foliage and fruit of my new variety, with the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown in Wasco, Calif., with color terminology based on the Nickerson Color Fan by Munsell Color Company, except where general color terms of ordinary dictionary significance are adequately definitive.

TREE

The tree is upright-spreading in habit, dense and very productive; it is moderately vigorous. Current growth is smooth and of average caliper. Moderately old wood is moderately smooth and has numerous medium-size lenticels. Old wood is also moderately smooth and has numerous medium-size lenticels and occasional deep longitudinal fissures.

The leaves of this new variety may be grouped in Class 3 of the Meader & Blake system[1], since they are "wavy and crinkled." Foliage is abundant. Average leaf sizes range from 15 to 16.5 centimeters in length and from 3.5 to 4.3 centimeters in width. The leaves are lanceolate with acuminate apices, and are of medium thickness. The upper surface of the leaves is dark green in color while the lower surface is lighter green. Petioles are of medium length and medium thickness. Leaf margins are finely serrate. About 4 small glands — mostly reniform — appear on the petiole and/or on the base of each leaf blade. Glands are green in color and are arranged alternately.

[1]Meader & Blake: Progress Report on Identification of Peach Varieties by Leaf Characteristics, vol. 37 (1939 Proceedings) American Society for Horticultural Science, pages 203–207.

BLOOM

Flower buds in the "pink bud" stage show color near Strong Red, 5R4/12. Fully open flowers are between Strong Red, 5R4/12, and Deep Pink, 10RP5/12, in color. The dates of first and full bloom vary from about February 20 to about March 5 and from about March 5 to about March 20, respectively, due to weather variations from year to year.

When fully open, the flowers are large, double and quite showy, usually from about 4 to about 5 centimeters in diameter, with adequate winter pruning of the tree. Individual blooms comprise usually from 14 to 18 petals, occasionally with a few petaloids.

The petals are arranged regularly, are cupped and sometimes wavy, while the petaloids are twisted and/or irregular. Petals are broadly obovate and are rounded at the apex and near the base, but tapering toward the point of attachment.

From 1 to 4 flowers appear at nearly every node with the nodes usually spaced from 1 to 2.5 centimeters apart on flowering branches, thereby forming an almost continuous spray of flowers along each branch giving the tree a definite ornamental appearance during the blooming period.

FRUIT

The fruit usually begins to ripen in mid-July at Wasco, Calif., but varies slightly from year to year because of varying weather conditions, and continues to ripen and hold on the tree for a period of several weeks. When eating-ripe, the fruits on the tree are reasonably uniform in size, ranging from medium to large when properly thinned. In axial diameter individual fruits measure from about 6.8 centimeters to about 7.2 centimeters. In transverse diameter both in the suture plane and at right angles to the suture plane the fruits measure from about 7 centimeters to about 8 centimeters. The fruits are uniform to slightly variable in shape, being most symmetrical and globose.

The suture appears usually as a shallow, but distinct line extending from the base to the apex along the ventral surface of the fruit with a slight depression beyond the pistil point. The ventral surface is rounded and sometimes slightly lipped toward the base, with the lips slightly unequal. The stem cavity is flaring and slightly elongated in the suture plane with the suture showing on one side. The depth of the cavity ranges from about 11 millimeters to about 14 millimeters. The base of the fruit is rounded to somewhat truncate and its apex short, with a short, apical pistil point.

The stem has a medium adherence to the stone and measures about 8 millimeters to about 10 millimeters in length. It is stout and glabrous.

The skin, medium in thickness and toughness, is slightly bitter, but parts relatively easily from the flesh. It has a moderate amount of pubescence of short length which rolls up when rubbed. The skin color is generally between Moderate Orange Yellow, 10YR8/10, and Moderate Orange Yellow, 7.5YR8/8, overlaid with near Dark Red, 5R3/7, over about ¼ to ⅓ of its surface.

The flesh is moderately firm, melting and of fine texture with abundant, relatively fine, tender fibers. It has a pronounced aroma and a strong sweet and subacid flavor. Its juice is rich and abundant. The eating quality is good, especially for home use. The color of the flesh is between Moderate Orange Yellow, 10YR8/10, and Strong Orange Yellow, 10YR7/10, and the surface of the pit cavity is lightly to moderately colored with near Strong Red, 5R4/12.

STONE

The stone is free, except for a slight adherence to the flesh along both ventral edges toward the base; sometimes short, fiber-like threads are retained along the ridges and in some of the pits. The stone is of medium size: its length ranges from about 32 to about 36 millimeters; its width and its thickness, both from about 24 to about 28 millimeters.

The form of the stone is oval, but somewhat cuneate toward the apex. The base is oblique, the hilum narrowly oval, and the apex acute. The sides of the stone are unequal, being flattened on one side, and the surface is irregularly furrowed along the ventral edge, ridged near the base and along the dorsal edge, and pitted throughout. The ridges are jagged toward the base. The pits are circular or elongated. The ventral edge is of medium thickness and without wings toward the base. The dorsal edge is of medium thickness and has a shallow, narrow groove throughout its length while the ridges on either side are interrupted.

The color of the stone is between Strong Red, 5R4/12, and Moderate Reddish Brown, 10R3/4.

The fruit is well adapted for home use since it ripens over a period of several weeks, holds well on the tree and has desirable dessert-fruit qualities, but it is deficient in the shipping qualities desired in market peaches. It does have good resistance to such insects and diseases as most commonly attack peach trees and their fruits in Southern California.

I claim:

1. A new and distinct variety of peach tree which combines desirable fruit-bearing qualities with attractive ornamental flowering characteristics, substantially as herein shown and described, characterized particularly as to novelty by its combination of large double flowers of a medium red to deep pink coloration with from about 1 to 4 flowers per node and with the nodes relatively closely spaced, giving the tree a distinctive and highly ornamental appearance during the blooming period; large yellow-fleshed, freestone fruit of melting texture, which has a well balanced relatively strong peach flavor and a ripening period generally beginning in mid-July and continuing through early August in the San Joaquin Valley of California, said tree further having foliage which is "wavy and crinkled," corresponding to class 3 of the Meader & Blake system.

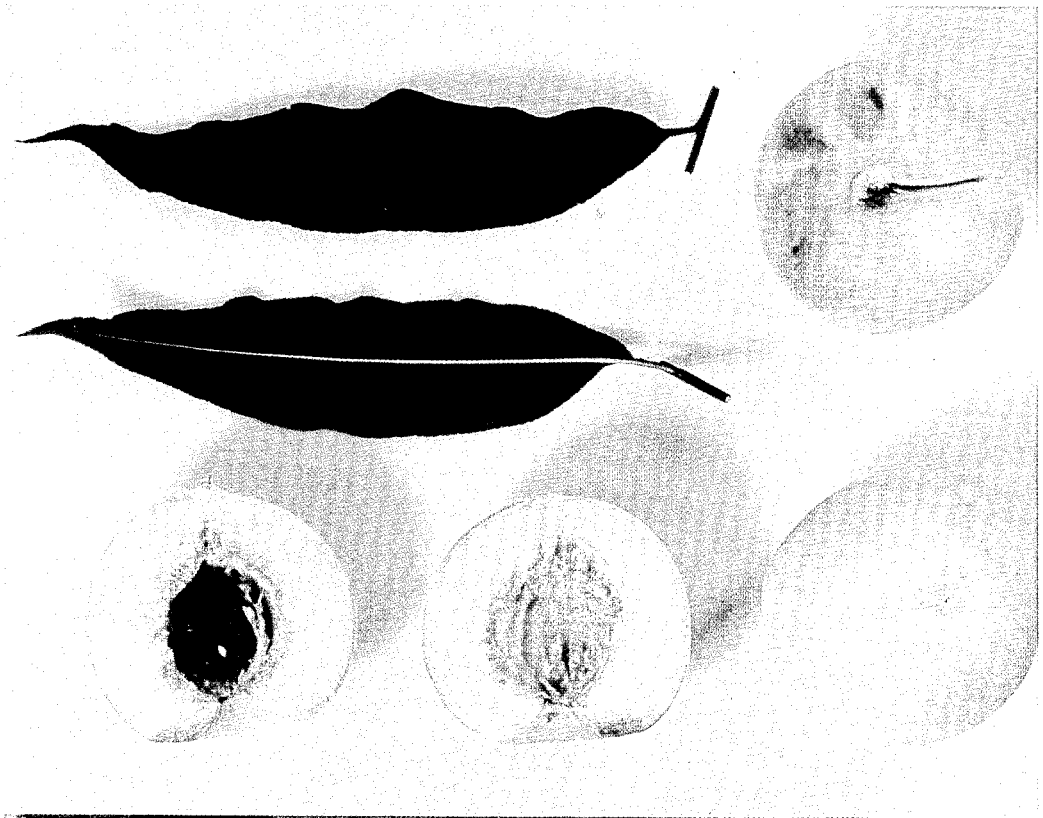
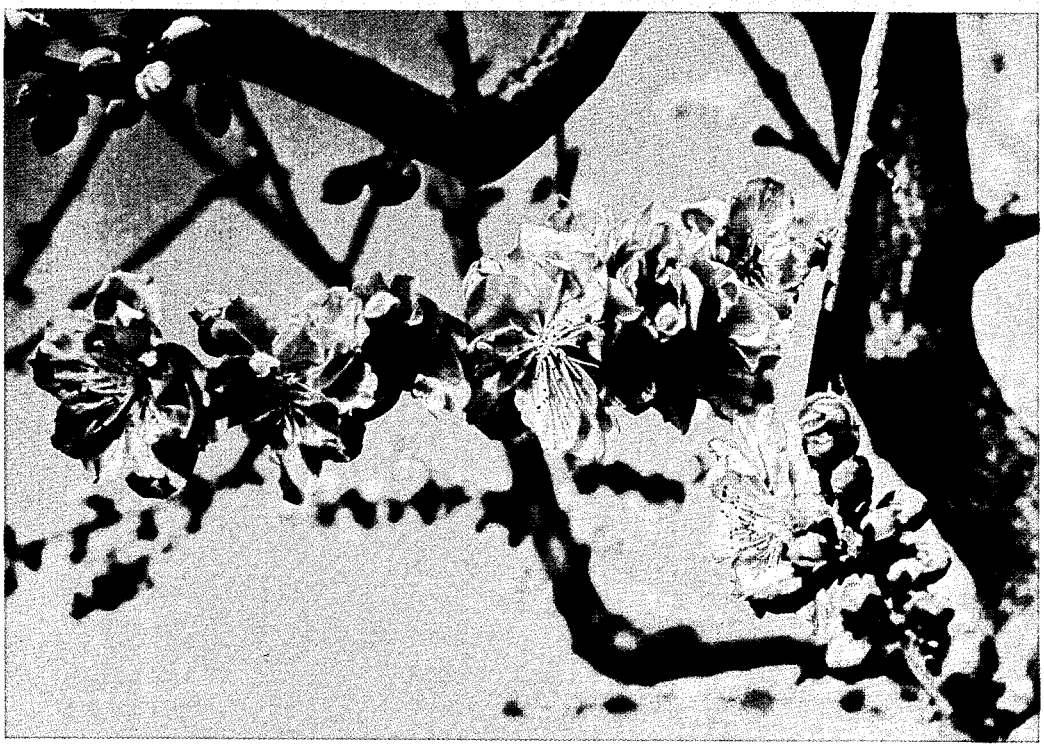

* * * * *